(12) United States Patent
Holland et al.

(10) Patent No.: US 7,315,377 B2
(45) Date of Patent: Jan. 1, 2008

(54) SYSTEM AND METHOD FOR REMOTE SENSING AND/OR ANALYZING SPECTRAL PROPERTIES OF TARGETS AND/OR CHEMICAL SPECIES FOR DETECTION AND IDENTIFICATION THEREOF

(75) Inventors: Stephen Keith Holland, Charlottesville, VA (US); Roland H. Krauss, Charlottesville, VA (US); James M. Childers, IV, Yorktown, VA (US); Gabriel Laufer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 167 days.

(21) Appl. No.: 10/544,421

(22) PCT Filed: Feb. 10, 2004

(86) PCT No.: PCT/US2004/003801

§ 371 (c)(1),
(2), (4) Date: Aug. 4, 2005

(87) PCT Pub. No.: WO2005/050163

PCT Pub. Date: Jun. 2, 2005

(65) Prior Publication Data

US 2006/0132780 A1 Jun. 22, 2006

Related U.S. Application Data

(60) Provisional application No. 60/446,301, filed on Feb. 10, 2003.

(51) Int. Cl.
*G01J 3/51* (2006.01)
*G01N 21/25* (2006.01)

(52) U.S. Cl. ............... 356/419; 250/226; 250/339.02; 250/339.07; 356/51; 356/418

(58) Field of Classification Search .............. 356/51, 356/416, 418, 419; 250/226, 338.5, 339.01, 250/339.02, 339.07
See application file for complete search history.

(56) References Cited

U.S. PATENT DOCUMENTS 3,667,850 A * 6/1972 Smith et al. .............. 356/419

(Continued)

FOREIGN PATENT DOCUMENTS

WO  WO 00/55602  9/2000

OTHER PUBLICATIONS

Stephen K. Holland, et. al., Demonstration of an uncooled LiTaO3-detector-based differential absorption radiometer for remote sensing of chemical, no date.

(Continued)

*Primary Examiner*—F. L. Evans
(74) *Attorney, Agent, or Firm*—Robert J. Decker

(57) ABSTRACT

A method and a low-cost, robust and simple system for remote sensing and analyzing spectral properties of targets as a means to detect and identify them is introduced. The system can be highly portable but is usable in fixed locations or combination thereof. An aspect of the method and system includes the capability to distribute, modulate, aperture and spectrally analyze radiation emitted or absorbed by a volumetric target chemical species (solid, liquid or gas) or a target surface. Radiation is first collected by a single light gathering device, such as a lens, telescope, or mirror, and then distributed to multiple detectors through spectrally discriminating components and if desired through apertures to achieve this desired detection and identification.

106 Claims, 10 Drawing Sheets

U.S. PATENT DOCUMENTS

| | | | |
|---|---|---|---|
| 3,869,212 A * | 3/1975 | Burcher et al. .............. | 356/419 |
| 3,955,891 A | 5/1976 | Knight et al. | |
| 4,669,817 A | 6/1987 | Mori | |
| 4,778,988 A | 10/1988 | Henderson | |
| 4,790,654 A | 12/1988 | Clarke | |
| 4,980,547 A | 12/1990 | Griffin | |
| 5,128,797 A | 7/1992 | Sachse et al. | |
| 5,210,702 A | 5/1993 | Bishop et al. | |
| 5,319,199 A | 6/1994 | Stedman | |
| 5,338,933 A | 8/1994 | Reeves et al. | |
| 5,371,367 A | 12/1994 | DiDomenico et al. | |
| 5,401,967 A * | 3/1995 | Stedman et al. .......... | 250/338.5 |
| 5,473,438 A * | 12/1995 | Keranen et al. ............. | 356/419 |
| 5,479,258 A | 12/1995 | Hinnrichs et al. | |
| 5,489,777 A | 2/1996 | Stedman | |
| 5,498,872 A | 3/1996 | Stedman | |
| 5,585,622 A | 12/1996 | Durst et al. | |
| 5,886,247 A | 3/1999 | Rabbett | |
| 5,930,027 A | 7/1999 | Mentzer et al. | |
| 6,057,923 A | 5/2000 | Sachse | |
| 6,064,488 A | 5/2000 | Brand et al. | |
| 6,111,248 A | 8/2000 | Melendez et al. | |

OTHER PUBLICATIONS

Gabriel Laufer, "Optimized differential absorption radiometer for remote sensing of chemical effluents," Applied Optics, vol. 41 (No. 12), p. 2263-2273, (Apr. 20, 2002).

* cited by examiner

SYSTEM AND METHOD FOR REMOTE SENSING AND/OR ANALYZING SPECTRAL PROPERTIES OF TARGETS AND/OR CHEMICAL SPECIES FOR DETECTION AND IDENTIFICATION THEREOF

CROSS-REFERENCE TO RELATED APPLICATIONS

This application is a national stage filing of International Application No. PCT/US2004/003801, filed on Feb. 10, 2004, which claims benefit under 35 U.S.C. Section 119(e) of the earlier filing date of U.S. Provisional Application Ser. No. 60/446,301, filed Feb. 10, 2003, entitled "Method and System for Radiation Modulation and Distribution to Multiple Detectors," which are hereby incorporated by reference herein in their entirety.

The present application is also related to International Application No. PCT/US00/04027, filed Feb. 18, 2000, entitled "Passive Remote Sensor of Chemicals," and corresponding U.S. application Ser. No. 09/936,833, now U.S. Pat. No. 6,853,452 issued Feb. 8, 2005, of which are assigned to the present assignee and are hereby incorporated by reference herein in their entirety.

FIELD OF THE INVENTION

The present invention relates generally to a method and system for remote sensing and/or analyzing spectral properties of targets and/or chemical species as a means to detect and identify them.

BACKGROUND OF THE INVENTION

Over the past several years, optical sensors have proven to have broad applicability in the remote measurement of physical, chemical, and biological phenomena. Such sensors can be used to measure a wide range of variables including but not limited to temperature, pressure, force, flow, radiation, liquid level, pH, displacement, humidity, vibration, strain, rotation, velocity, magnetic and electric fields, acceleration, acoustic fields, and to detect the presence of and identify one or more chemical species. In addition to this wide range of potential uses, optical sensors have a number of other benefits. For example, they are often small, compact, light and have a longer lifetime than other types of sensors. Optical sensors also tend to be immune to electromagnetic interference, can be electrically isolated, and often have high sensitivity. As a result, these sensors are not only replacing conventional sensors in many areas in science, engineering, and medicine but researchers are beginning to create new kinds of sensors that have unique properties. Since remote sensors do not require direct contact with the measured target nor do they require sampling of any chemical, they provide the ability to scan large areas and volumes in a short period of time.

There is utility and demand for optical sensors in an array of industries. Environmental and atmospheric monitoring, earth and space sciences applications, industrial chemical processing and biotechnology, law enforcement, digital imaging, scanning, and printing are a few examples. In addition to these more established uses, there is an ever increasing need for devices and methods capable of early, passive, and remote detection of dangerous gases and other substances, particularly for security applications, but also for safety. Recently, the need for these systems has been heightened by the spread of chemical warfare technology around the world and the increasing number of acts of global terrorism, for example, threats against chemical plants can adversely impact large population centers in the vicinity of such plants. Indeed, the potential release of dangerous substances is now a serious concern not only for the military, but domestically as well. The ability of remote sensors to probe large volumes quickly and without actually entering a chemical cloud provides obvious benefits to first responder and law enforcement agencies.

The development of passive remote detectors has also been driven by other factors, such as the growing concern regarding the effects of industrial and vehicular emissions as well as other forms of environmental pollution like pesticide over application. Remote detectors are also needed to monitor and study long-term trends as well as to identify and provide warnings regarding day-to-day environmental problems that may affect the health of local and global populations.

Although many remote sensors, e.g., lidar based systems and Fourier transform interferometers, can meet most of these detection objectives, they are complex, expensive, large and heavy. There is a strong and unmet need for low-cost, highly portable and robust devices. For example, in many domestic security applications it is desired that each police car or fire truck include a sensitive remote sensor of chemicals that can be hand carried by its crew to the site of potential incidents and operated without actually endangering its operator. Similarly, public buildings require advanced warning to protect occupants against chemical threats released indoors or outdoors. The cost of such a sensor must meet the needs of local government authorities and the level of complexity and training must meet the ability of police officers or firefighters.

In some optical remote sensing devices, designed to provide low-cost, robust and simple systems (e.g., differential absorption radiometer—DAR), a method of collecting, modulating, and distributing (i.e., multiplexing) light to multiple detectors is required. Here light is used to describe all types of electromagnetic radiation, including but not limited to x-rays, ultraviolet, visible, infrared and microwave radiation. In such applications, multiple detectors are often fitted with different filters (e.g., bandpass, notch, long pass, short pass, diffractive, or polarizers), for spectral analysis of a target. Further, many types of detectors must receive an amplitude modulated signal to optimize their response (e.g., pyroelectric detectors) or to reduce noise and enhance detectivity by allowing for detection by demodulation in the frequency domain. While multiplexing,. i.e. providing a coincident field of view (FOV) for multiple detectors, may be achieved with the use of multiple lenses, split lenses, or various configurations of polarizers or split mirror, each of these techniques requires precise alignment of the optical components for each detector thereby increasing complexity and cost and making the system susceptible to misalignment by vibration, mild shocks, temperature variations, acoustics etc. thereby rendering them inadequate for their intended applications. Further, these techniques do not provide modulation of the collected radiation and reduce the available radiation by 1/N where N is the number of detectors. Radiation modulation is typically achieved by either spinning wheel or tuning fork choppers, or polarization modulators which must then be added to the already complex multiplexed system. Both modulation techniques block radiation for a certain fraction of the modulation cycle, thereby reducing the collection and light management efficiency. Typical mechanical modulators use a 50% duty cycle (closed 50% of the time).

Thus, there is a need in the art for a simple, robust and low-cost method and system for simultaneous multiplexing and modulation that may include placing multiple detectors behind a large single lens, distributing, modulating, aperturing, and spectrally analyzing the collected optical signal among the detectors by sequentially illuminating the detectors through a masking system and spectrally resolving components such as bandpass, notch, long pass, short pass, diffractive, or polarizers. In this case, detectors are illuminated at full collection intensity, but for a fraction of the duty cycle, allowing the signal to be recorded only when an individual detector is illuminated by radiation from the target while avoiding noise from being recorded when that detector is not illuminated. Also, by densely packing the detectors in linear, circular, or ring type arrays (thus reducing space between adjacent detectors), sequential illumination can reduce radiation loss only to periods when radiation falls within the small spaces between the adjacent detectors.

SUMMARY OF THE INVENTION

The present invention generally relates to a method and a low-cost, robust and simple system for remote sensing and analyzing spectral properties of targets as a means to detect and identify them. The system may be portable, including man portable (such as, but not limited thereto, a hand held device or personnel mounted) or it may be fixed location mounted or vehicle mounted. An aspect of an embodiment of the present invention includes a method and system to distribute, modulate, aperture and spectrally analyze radiation emitted or absorbed by a volumetric target chemical species (solid, liquid or gas) or a target surface. Radiation is first collected by a single light gathering device, such as a lens, telescope, or mirror, and then distributed to multiple detectors to achieve this desired detection and identification. This type of light distribution and modulation is useful, for example, in applications where multiple detectors are required to observe the same scene while at the same time having the incident signal modulated in time.

It should be appreciated that light, as mentioned through out this document, should be interpreted to include all types of electromagnetic radiation, including but not limited to infrared radiation, far-infrared radiation, microwave radiation, x-ray radiation, ultraviolet radiation, visible radiation, or any radiation that can be focused.

In one such application, each detector is equipped with a spectral filter, and by distributing the radiation between these detectors as described in the disclosure of the present invention, multi-spectral characteristics of the target area can be measured. The time dependent modulation allows frequency domain, gated or windowed detection and the use of low-cost detectors that require transient input (e.g., pyroelectric detectors). Multiple radiation detectors are arranged with small or no physical space between them either in a circular pattern (e.g., on a disk or the like), ring pattern (i.e., facing inward or outward of the circle), or in a linear or curved array. Either a spinning or rotating mirror or lens, a mirror oscillating around a pivot, or a linearly oscillating lens or detector array is used to distribute the incoming signal to these detectors. One section of the detection area may be left empty. When operation of the system is stopped, the mirror or lens may be pointed ("parked") towards the empty area to protect the system from excess exposure (e.g., when facing the sun, but not limited thereto).

Since each detector is exposed to radiation for only a fraction of the spinning or oscillating cycle time, the output of each detector is modulated. Since the gap between the detectors of the array can be made small or non-existent, most of the radiation collected by the light gathering device throughout the entire scanning cycle must fall on the active area of the detector array. Thus, unlike chopper-based systems, where radiation would normally be blocked by the chopper blades, this system can achieve nearly complete use of the collected radiation. A synchronous demodulation process is then utilized to detect the signal in the time domain and separate the desired signal (which is located in the time domain during a known phase of the spinning or oscillating cycle or in the frequency domain at the known spinning or oscillating cycle frequency) from the composite signal.

An aspect of an embodiment of the present invention provides an integrated radiation gathering, modulation and distribution system for the remote, passive detection of chemical species or other desired or required targets or portions of targets and/or chemical species. In an aspect, the system can detect one or more chemical species or other targets without an active source of radiation independent from that produced by the species or the other target themselves and reliably separate the radiation emitted by the target species from that emitted by the optical equipment used for measurement.

An aspect of an embodiment of the present invention includes a system for remote sensing and analyzing spectral properties of at least one target and/or chemical species. The system comprising: a) a light gathering device that collects and focuses incoming radiation emitted and/or absorbed and/or scattered by the target and/or chemical species to be analyzed; b) a folding optical element for directing the collected and focused radiation from the light gathering device to at least one of a plurality of detectors; c) at least one spectrally discriminating optical element in front of at least some of the detectors for spectrally resolving the collected radiation; d) wherein, the detectors, in relative movement with the folding optical element, producing an output signal; and e) a driving device to produce the relative movement; f) a device or method to monitor phase and frequency of the relative movement; and g) a demodulation device, synchronous with the driving device, to demodulate the output signal produced by the detectors.

An aspect of an embodiment of the present invention includes a system for remote sensing and analyzing spectral properties of at least one target and/or chemical species. The system comprising: a) a light gathering device that collects, focuses, and directs incoming radiation emitted and/or absorbed and/or scattered by the target and/or chemical species to be analyzed to one of a plurality of detectors; b) at least one spectrally discriminating optical element in front of at least some of the detectors for spectrally resolving the collected radiation; c) the detectors, in relative movement with the light gathering device, producing an output signal; d) a driving device to produce the relative movement between the light gathering device and the detectors; e) a device or method to monitor phase and frequency of the relative movement; and f) a demodulation device, synchronous with the driving device, to demodulate the output signal produced by the detectors.

An aspect of an embodiment of the present invention includes a method for remote sensing and analyzing spectral properties of at least one target and/or chemical species. The method comprising: a) collecting and focusing incoming radiation emitted and/or absorbed and/or scattered by the target and/or chemical species to be analyzed, the collecting and focusing being conducted from a gathering location; b) directing the focused radiation, the directing being conducted at a directing location; c) spectrally analyzing the collected radiation at a spectral analysis location, the spectral analysis produces spectral signature that can be used to identify target; d) detecting the directed and spectrally analyzed radiation at a detecting location, wherein the directing location and the detecting location is in relative movement from one another, the detection producing an output signal; e) monitoring the phase and frequency of the relative movement; and f) demodulating the output signal.

An aspect of an embodiment of the present invention includes a method for remote sensing and analyzing spectral properties of at least one target and/or chemical species. The method comprising: a) collecting, focusing, and directing incoming radiation emitted and/or absorbed and/or scattered by the target and/or chemical species to be analyzed, wherein the collecting, focusing, and directing being conducted from a gathering location; b) spectrally analyzing the collected radiation at a spectral analysis location, the spectral analysis produces spectral signature that, can be used to identify target; c) detecting the directed and spectrally analyzed radiation at a detecting location, wherein the gathering location and the detecting location is in relative movement from one another, the detection producing an output signal; d) monitoring the phase and frequency of the relative movement; and e) demodulating the output signal.

Further, an aspect of the methods and systems may include a processor wherein said processor receives output signals from the detectors and/or demodulation device to separate background effects and noise from output signal to provide a net output that represents the spectral characteristics of the target and/or chemical species and use those characteristics to detect and/or identify the targets and/or chemical species. The detected and/or identified targets and/or chemical species are provided for at least one of: reducing or eliminating danger in public, private or military facilities or spaces or outdoors due to the presence of toxic chemicals, to allow control of chemical or medical manufacturing processes, or to allow control or monitoring of pollution or other processes due to plant or factory emission or other equipment. The system can be at least partially disposed in a housing defined as hand held device (palm device, suitcase, pack, wrist attachment, etc.), portable device, fixed location mounted, vehicle mounted, or robotic mounted or personnel mounted (helmet, pack, belt, back pack, clothing, weapon mounted, etc.). It should be appreciated that signals provided for communications interfacing between modules or there within may be a variety of communications paths or channels. Such implementations include, but not limited thereto, hardware, semiconductors, integrated circuits, wire or cable, fiber optics, phone line, a cellular phone link, an RF link, an infrared link, BLUE TOOTH, and other communications channels.

These and other objects, along with advantages and features of the invention disclosed herein, will be made more apparent from the description, drawings, and claims that follow.

BRIEF DESCRIPTION OF THE DRAWINGS

The foregoing and other objects, features and advantages of the present invention, as well as the invention itself, will be more fully understood from the following description of potential embodiments, when read together with the accompanying drawings in which.

DETAILED DESCRIPTION OF THE INVENTION

Figure 1:
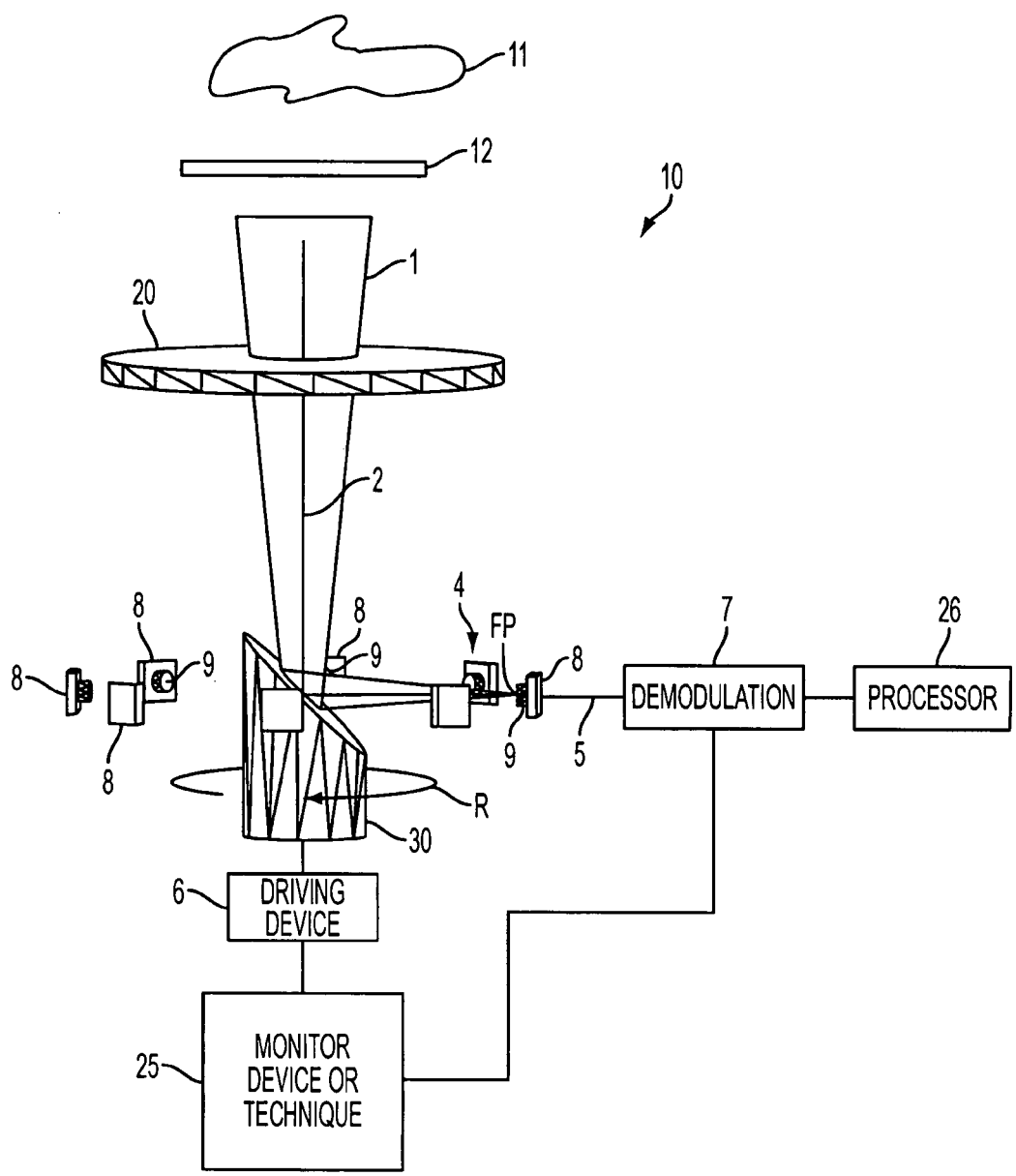
FIG. 1 schematically illustrates an embodiment of the present invention system for remote sensing and analyzing spectral properties of targets, wherein a light gathering device is in optical communication with a folding optical element, such as a reflecting mirror, tilted at a large reflection angle such that the incoming collected and focused radiation is directed to the detector array.
Figure 2:
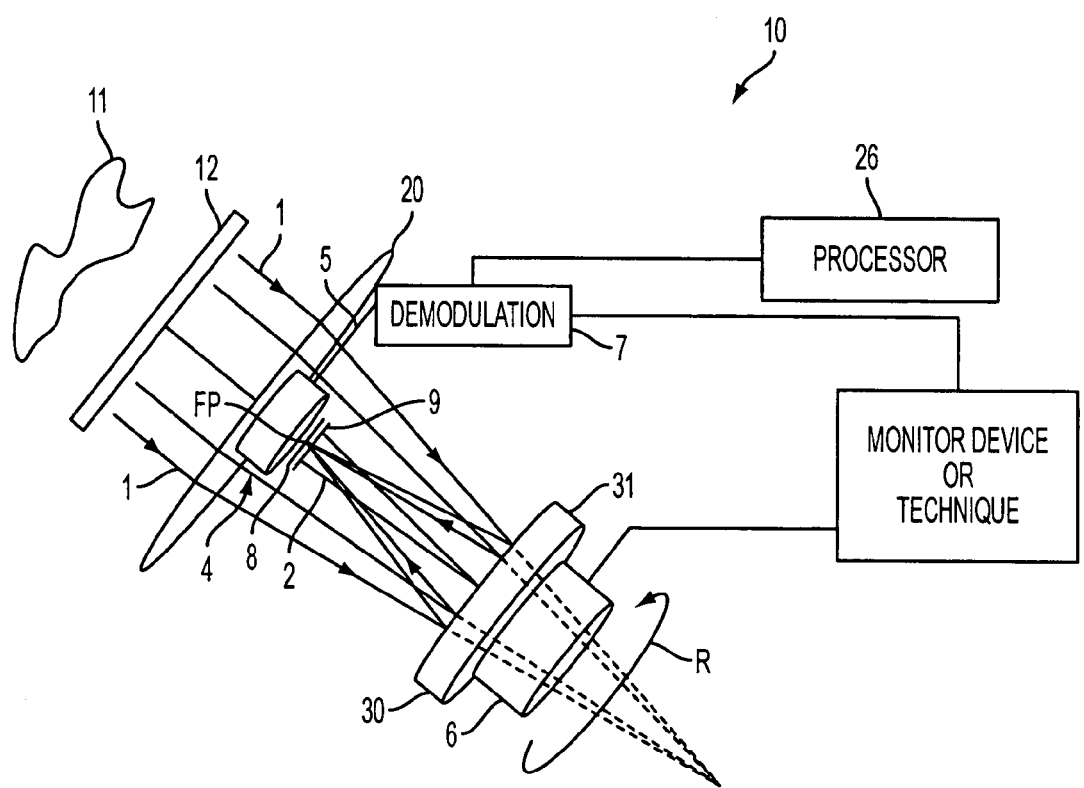
FIG. 2 schematically illustrates an embodiment of the present invention system for remote sensing and analyzing spectral properties of targets, wherein a light gathering device is in optical communication with a folding optical element, such as a reflecting mirror, tilted at a small reflection angle such that the incoming collected and focused radiation is directed to the detector array.

Referring to FIG. 1, FIG. 1 schematically illustrates an embodiment of the present invention system for remote sensing and/or analyzing spectral properties of targets as a means to detect and identify them. An embodiment of the system 10 includes a light gathering device 20, which collects and focuses incoming radiation 1 emitted directly by the target or radiation from an illuminating source partially absorbed by the target and/or chemical species 11 to be analyzed. A folding optical element 30 directs this collected and focused radiation from the light gathering device 20 to an array 4 of detectors 8. A spectrally discriminating optical element 9 is in front of or in the optical path of at least some of the detectors 8 for spectrally resolving the collected radiation. Some examples of spectrally discriminating optical elements 9 include, but not limited thereto, bandpass filters, notch filters, long and short pass filters, diffraction elements, polarizer filters, or combination thereof, etc. The folding optical element 30 is a mirror, tilted at a large reflection angle (whereby large reflection angle is defined as the tilt angle of the mirror required to project the axial ray 2 of the incoming radiation 1 away from the on-axis focusing cone of the light gathering device 20 as in FIG. 1. Similarly, a small reflection angle is defined as any tilt angle of the mirror which will result in projecting the axial ray 2 of the incoming radiation 1, into its own path as defined by the on-axis focusing cone of the light gathering device 20 as shown in FIG. 2) or reflection angle(s) as required or desired to direct the radiation away from the collection cone of the light gathering device 20 that reflects radiation towards the detectors, which are arranged on an array that is configured as a ring with the sensitive detecting element facing inward towards the radiation cone. With this configuration, the detectors do not block incoming radiation. These multiple detectors 8 can be arrayed with small or no physical space between them either in a ring pattern, as shown, or as will be discussed later, in a circular pattern, curved pattern or linear array. In addition to this embodiment and embodiments discussed throughout this document, it should be appreciated that the number of individual detectors can be increased or decreased and may be comprised of varying sizes and types. Thus, it is preferred that the radiation collected by the light gathering device 20 must fall sequentially on at least one of the detectors 8 throughout the scan, achieving nearly complete use of the incoming radiation 1. This increases the signal to noise ratio and sensitivity. The aperture device 12 is optional when desired or required and can be placed on either the target side (front) of the gathering device 20 or the detector side (behind) of the gathering device.

It should be appreciated that an embodiment could scan one detector(s) for, say 90% of the time or as desired or required, move the beam off it for just long enough to get a reference reading, then put the beam back on it, thereby achieving nearly complete use of the incoming radiation.

It should be appreciated that any lens, mirror, aperture device, mask or filter mentioned in this document, as well as detector arrays, may be a variety of shapes and sizes. The surfaces of the lenses, mirrors, filters, arrays may be planar or curved (concave or convex), symmetrical, or asymmetrical, as well as having multiple contours and faces on its surface.

It should be appreciated that light, as mentioned through out this document, should be interpreted to include all types of electromagnetic radiation, including but not limited to infrared radiation, far-infrared radiation, microwave radiation, x-ray radiation, ultraviolet radiation, visible radiation, or any radiation that can be focused. In an embodiment, the radiation incident on the array of detectors 8 is modulated because the detectors 8 and the optical element 30 are in relative movement. This movement or rotation is produced by a driving device 6 (or other desired mechanism or technique) that is in communication with the folding optical element 30 as shown by the rotation arrow referenced as R or alternatively the detector array 4 may rotate (not shown) or both optical element and detector array may be in relative motion (not shown). A monitoring device 25 or monitoring method such as software or hardware or combination thereof is in communication with the system, or as the example shown in FIG. 1 with the driving device, to monitor the phase and frequency of the optical element (and/or detector array). In FIG. 1, the driving device 6 is shown driving the optical element 30. It should be noted that the light gathering device 20 and folding optical element 30 are arranged in such a way that nearly all of the radiation 1 emitted by, or passed though (i.e., emitted, scattered, or partially absorbed by), the species or target 11 to be detected or analyzed, is focused on one detector 8 in the detector array 4 at a time. Thus, the detector array 4 is located at a distance from the light gathering device 20 that coincides or nearly coincides with the focal plane FP of the light gathering device 20 as reflected by the folding optical element 30. In summary, in one approach, multiple detectors are arranged in a ring pattern (or desired pattern) and placed such that, when the mirror is rotated about its center axis, the focal point of the incoming radiation 1, and thus the image of the target scene 11, moves successively to the detectors 8 on the array 4. In this manner, incoming radiation from the target, is distributed to one detector at a time until all detectors are exposed to the image after a complete revolution of the optical element or mirror.

The driving device 6 selects which individual detector the incoming radiation is focused on. By using a digitally controlled motor (e.g., a stepping motor) or a continuous motor with an analog or digital encoder, it is possible to control the amount of time the radiation is focused on any given detector 8 in the detector array 4 or the exposure sequence between the detectors (e.g., skip or repeat exposure to certain detectors). A symmetrical, constant velocity configuration involves illuminating each detector for the same amount of time. However, in other applications, for example, when the response of one of the detectors is low (or when desired), the incoming radiation may be focused on that detector for a longer period than the other detectors. Alternatively, more than one section of the detector may be exposed at a given time. Similarly, it may be possible to fully skip some detectors, or expose some detectors more than once during any cycle if necessary. In addition, one section or more of the detector array 4 may be left empty. As such, the space left empty (e.g., without any active detector) defines a gap (or a plurality of gaps), and towards which light can be directed when the sensor is not in operation. When operation of the system is stopped, the folding optical element may be pointed ("parked") such that the focal point is coincident with the empty area to protect the system when excess exposure is detected, predicted, or when desired. Each detector 8 can be fitted with different filters, such as spectral filters, if desired (e.g., bandpass, notch, long or short pass, diffractive, or polarizers) for analysis of different (e.g., multi-spectral) characteristics in a target material.

In response to the incident collected, focused, modulated, and directed radiation the detectors of the array 4 produce an output signal 5. This signal is demodulated by a demodulation device 7, synchronous with the driving device 6 that is causing either the folding optical element 30 or the detector array 4 to move with some known frequency. A synchronization signal may be provided to the demodulation device 7 by the monitor device 25, or other alternative means. This demodulation device 7 can accomplish the necessary demodulation by using up to two analog to digital (A/D) converters to monitor the "on" signal of two adjacent sensors while another converter may be required (depending on geometry) to monitor the "off" state of a non-illuminated sensor. Two A/D converters may be necessary for monitoring the on state of two adjacent sensors because, as the focal point location is changed, a portion of the focused radiation can fall on two adjacent sensors in optical sensor arrays where the inter-sensor spacing is significantly less than the radiation beam size. These multiple A/D channels may be implemented with a single A/D converter with an input channel multiplexer. Samples of the detector signals are taken while radiation is focused on them. The decision to monitor a detector can be based on the output of a stepper motor controller or an encoder. Reference samples, possibly acquired at a slower sample rate, are obtained from a detector, typically immediately preceding exposure to focused radiation. A microprocessor can then be used to compute the weighted average of the difference between the target-illuminated and reference signals of each detector, providing a usable baseband signal output proportional to the intensity of radiation reaching each sensor. Finally a processor 26 or the like is in communication with the system to process the signals, as desired or required from the detectors.

The light gathering device 20 may be a lens (e.g., refractive, Fresnel, GRIN, holographic, etc. and the like) as displayed in the figures but can also be a mirror or telescope. It may be necessary to aperture the light gathering device to prevent off-axis and unwanted radiation from entering the sensor. A number of different devices can be used to provide such aperturing whereby, for example, wherein the aperture device comprises an array of parallel optically transmitting channels or substantially parallel optically transmitting channels. For example a honeycomb consisting of a plate with multiple parallel optically transmitting channels can be placed immediately in front or behind the lens. By selecting the width and length of these channels, the field of view through the honeycomb can be designed to match the field of view of the sensor thereby providing blockage of off-axis radiation with minimal loss of on-axis radiation.

Alternatively, a mask consisting of an opaque disk or other shaped member having an aperture-like hole can be attached to the folding optical element 30. The mask can be aligned such that the radiation cone formed by the incoming radiation 1 behind the light gathering device 20 passes uninterrupted through the aperture while off axis radiation is blocked. By attaching the mask to the folding optical element 30, it can move with it, thereby providing in-phase aperturing and masking.

A number of different structures can act as the folding optical element 30. For example, the folding optical element 30 can be a mirror tilted at large reflection angle and located at the center of a ring array of detectors 8. This type of optical element is represented in FIG. 1. The driving device 6 can cause either the mirror or the detector array 4 to move, providing the desired distribution and modulation. It should be appreciated that the mirrors mentioned throughout this document may be at a variety of reflection angles as desired or required to provide illumination to detectors located outside the collection cone of the light gathering device 20.

Next, turning to FIG. 2, FIG. 2 schematically illustrates an embodiment of the present invention system for remote sensing and/or analyzing spectral properties of targets as a means to detect and identify them. The light gathering device 20 is in optical communication with the folding optical element 30 (which receives incoming radiation 1) that comprises a reflecting mirror 31, tilted at a small reflection angle, that is rotated by the driving device 6 or other mechanism as desired such that the incoming collected and focused radiation is directed to one of the detectors 8 in the circular detector array 4, which is located behind the light gathering device 20. In this configuration, the detector array 4 is smaller than the light gathering device 20, and therefore blocks only a fraction of the incoming focused radiation. Spectrally discriminating optical elements 9 may be placed in front of or in the optical path of at least some of the detectors 8 for spectrally resolving the collected radiation. Some examples of spectrally discriminating optical elements 9 include, but not limited thereto, bandpass filters, notch filters, long and short pass filters, diffraction filters, polarizer filters, etc. The mirror 31 is rotated by the driving device 6 as shown by the rotation arrow referenced as R or alternatively the detector array 4 may be rotated (not shown) or both may be rotated (not shown). For example, the detectors would rotate around the line of the axial ray near the focal point. A monitoring device 25 or monitoring method such as software or hardware or combination thereof is in communication with the system 10 to monitor the phase and frequency of the optical element (and/or detector array). Finally a processor 26 or the like is in communication with the system to process the signals, as desired or required from the detectors. The aperture device 12 is optional when desired or required and can be placed on either the target side (front) of the light gathering device 20 or the optical element side (behind) of the light gathering device, and can be either stationary or rotating with the mirror 31.

It should be appreciated that, although not shown, the detectors do not have to be in front of the lens. Rather, the mirror could both cycle the beam and, by angling, tilt it out of the line of the incoming radiation cone (off to the side of the lens).

Figure 3:
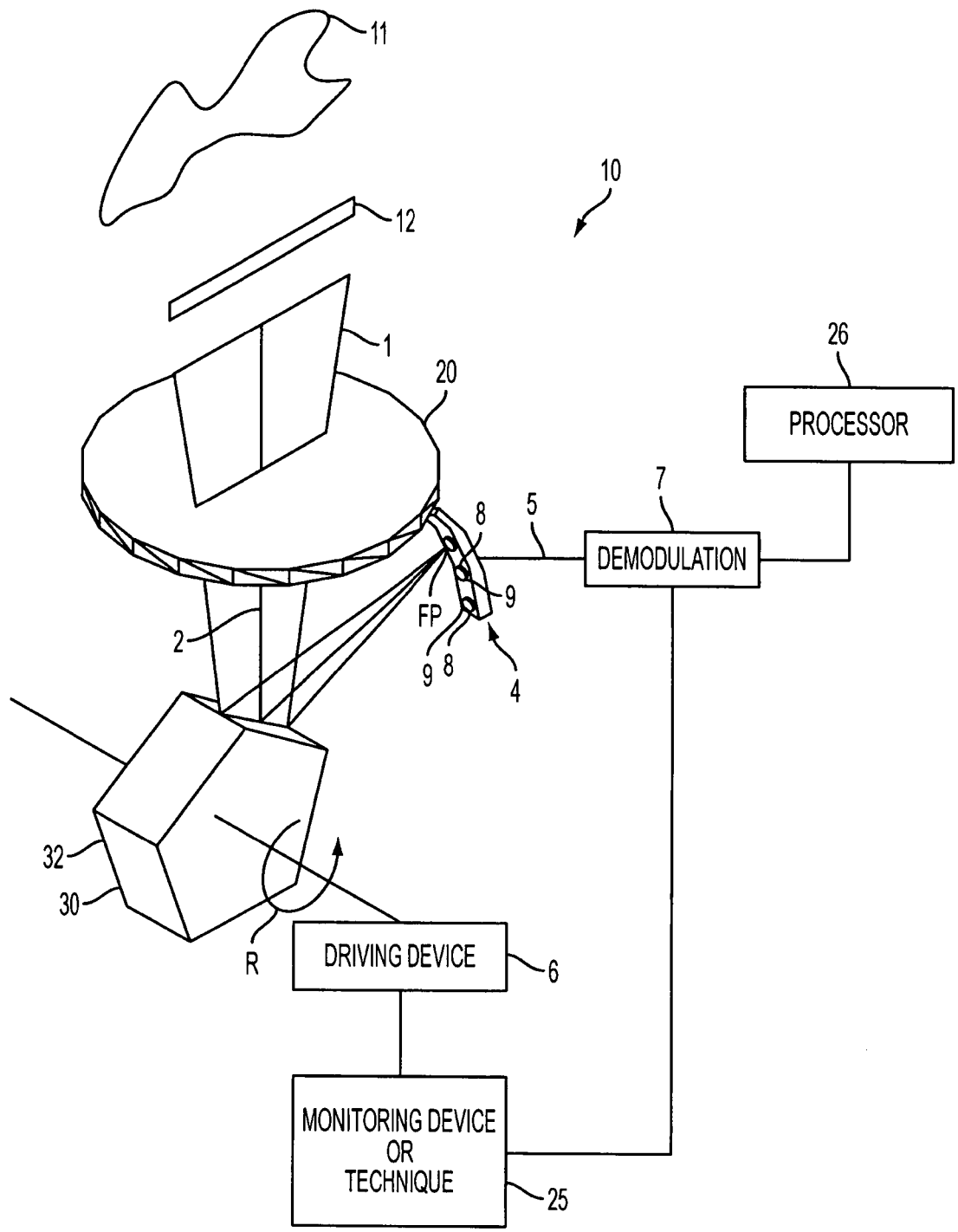
FIG. 3 schematically illustrates an embodiment of the present invention system for remote sensing and analyzing spectral properties of targets, wherein a light gathering device is in optical communication with a folding optical element, such as a reflecting multifaceted mirror, such that the incoming collected and focused radiation is directed to the detector array.

Next, turning to FIG. 3, FIG. 3 schematically illustrates an embodiment of the present invention system for remote sensing and/or analyzing spectral properties of targets as a means to detect and identify them. The folding optical element 30 can be a multifaceted mirror 32 spun by the driving device 6 or other mechanism as desired. The mirror may be rotated as shown by the arrow referenced as R. The detectors 8 are located in a semicircular or curved array 4 positioned such that as the driving device 6 spins the multifaceted mirror 32, the radiation focuses on each of the detectors 8 in sequence. Spectrally discriminating optical elements 9 are placed in front of or in the optical path of at least some of the detectors 8 for spectrally resolving the collected radiation. Some examples of spectrally discriminating optical elements 9 include, but not limited thereto, bandpass filters, notch filters, long and short pass filters, diffraction filters, polarizer filters, etc. In an approach, the spinning multifaceted mirror is used to focus radiation on the array of detectors arranged on a curved surface such that each detector is in or near the focal plane FP of the optical system. This configuration permits a rapid modulation rate with a relatively slow mirror spinning frequency. In addition, detectors can be placed outside the radiation path, thereby preventing blockage of the incoming radiation.

Figure 4:
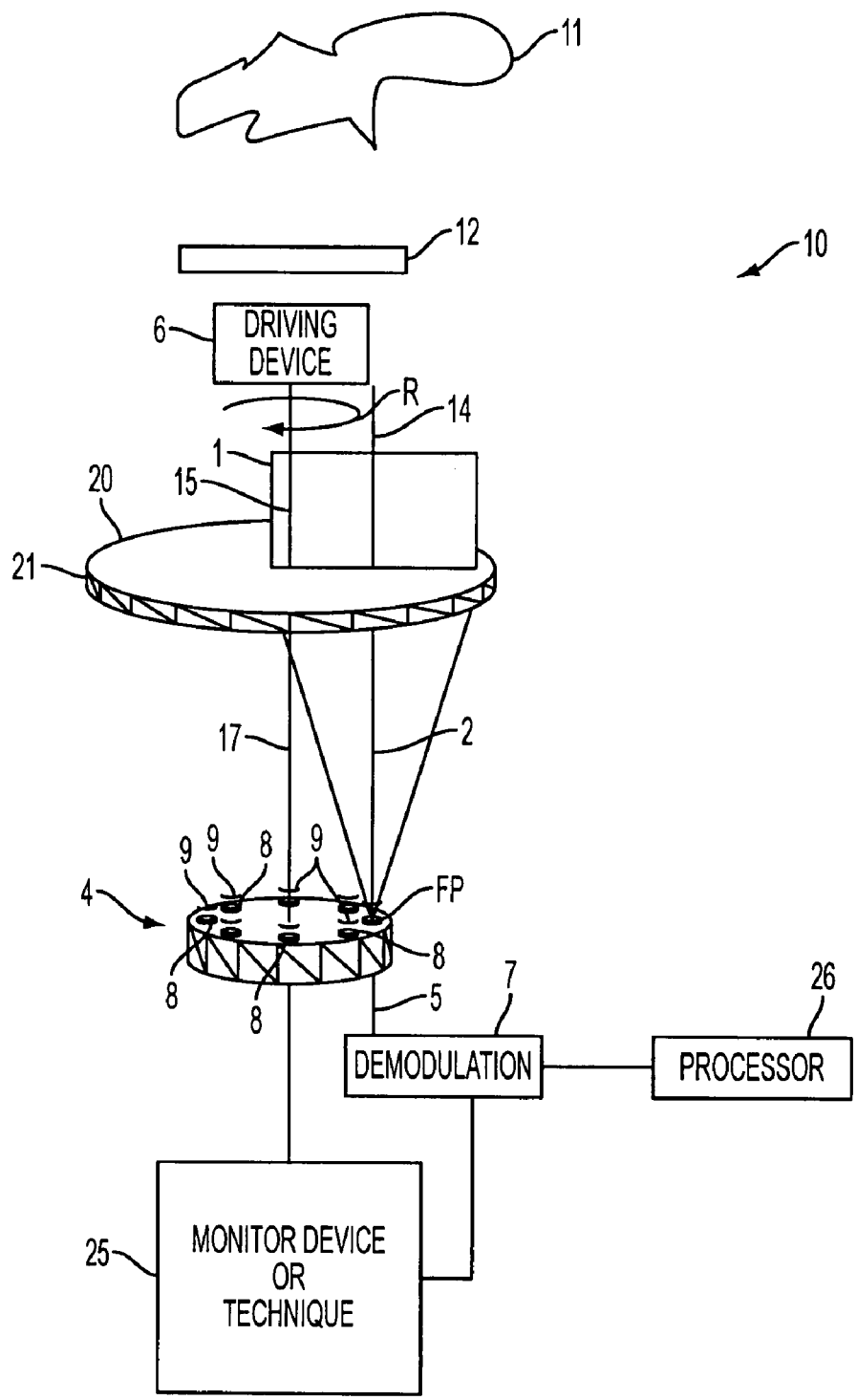
FIG. 4 schematically illustrates an embodiment of the present invention system for remote sensing and analyzing spectral properties of targets, wherein a light gathering device collects, focuses, and directs radiation emitted by the species or target to be detected or analyzed to an array of detectors, wherein a folding optical element is not necessarily included.

Next, turning to FIG. 4, FIG. 4 schematically illustrates an embodiment of the present invention system for remote sensing and/or analyzing spectral properties of targets as a means to detect and identify them. Unlike the embodiments discussed above in FIGS. 1-3, the folding optical element is not specifically included, although it should be appreciated that it may be added. The system 10 comprises a light gathering device 21 that collects, focuses, and directs radiation 1 emitted by the species or target 11 to be detected or analyzed to an array 4 of detectors 8. The detectors 8 are located in a circular shaped array 4 or other shape as desired or required. By directing the gathered radiation 1 directly to the individual detectors, the light gathering device 21 in FIG. 4 fulfills both the role of the light gathering device and folding optical element similarly illustrated in, for example, FIG. 1. Spectrally discriminating optical elements 9 are in front of or in the optical path of at least some of the detectors 8 for spectrally resolving the collected radiation. Some examples of spectrally discriminating optical elements 9 include, but not limited thereto, bandpass filters, notch filters, long and short pass filters, diffraction filters, polarizer filters, etc. The aperture device 12 is optional when desired or required and can be placed on either the target side (front) of the light gathering device 21 or behind the light gathering device, and can be either stationary or rotating with the light gathering device 21. Again, the detector array 4 is located at a distance from the light gathering device 21 that coincides or substantially coincides with the focal plane FP of the light gathering device 21. In an approach, to be discussed in greater detail below, the circular detector array 4 is placed in the focal plane of a lens with an off-axis focus and the lens is spun around an axis perpendicular to the lens that coincides with the axis of the circular detector array. An advantage of this approach is that, but not limited thereto, the spinning lens may be flat (e.g., when using Fresnel or holographic lens), thereby reducing aerodynamic drag below the level of the arrangement using an angled, rotating mirror. Another advantage is that the number of optical elements can be reduced below their number in the arrangement using an angled, rotating mirror thereby reducing cost and complexity. Off axis focus can be achieved by various methods, including using a holographic lens with one or more off axis focii or using a Fresnel lens with one or more off axis focii.

The radiation reaching the detector array 4 is modulated because the detector array 4 is in relative movement with the light gathering device 21. A driving device 6, with possibly the same characteristics described above, produces this relative movement. The driving device can cause either the light gathering device 21 to rotate as shown by the arrow of rotation referenced as R or alternatively the detector array 4 to rotate (not shown) or both (not shown). In FIG. 4, the driving device 6 is shown connected to the light gathering device 21.

Once exposed to radiation, the detectors 8 produce an output signal 5 that is directed to a demodulation device 7 which may operate in the same manner as described above. A number of different structures can be used as the light gathering device 21. In FIG. 4, the light gathering device 21 is a lens with an off-axis focus 14 (shown in FIG. 4 with a linear focal offset, but may also be angularly offset, as long as the FP of the lens rotates as to place the collected radiation sequentially on the detectors) spun around its own central axis by the driving device 6. The central rotational axis 15 of the lens 21 is aligned with the central axis 17 of the detector array 8, which is fixed, such that the source radiation 1, as focused by the lens 21, is incident on one of the individual detectors 8 at a time (or as per a desired or required sequence) having a lens focal axis referenced as 14. Alternatively, but not shown, the light gathering device, lens 21 and the detector array 4 can be arranged in the same way, but the lens 21 can be fixed and the detector array 4 can be rotated about its central rotational axis 17 by the driving device 6 or the like.

Figure 5:
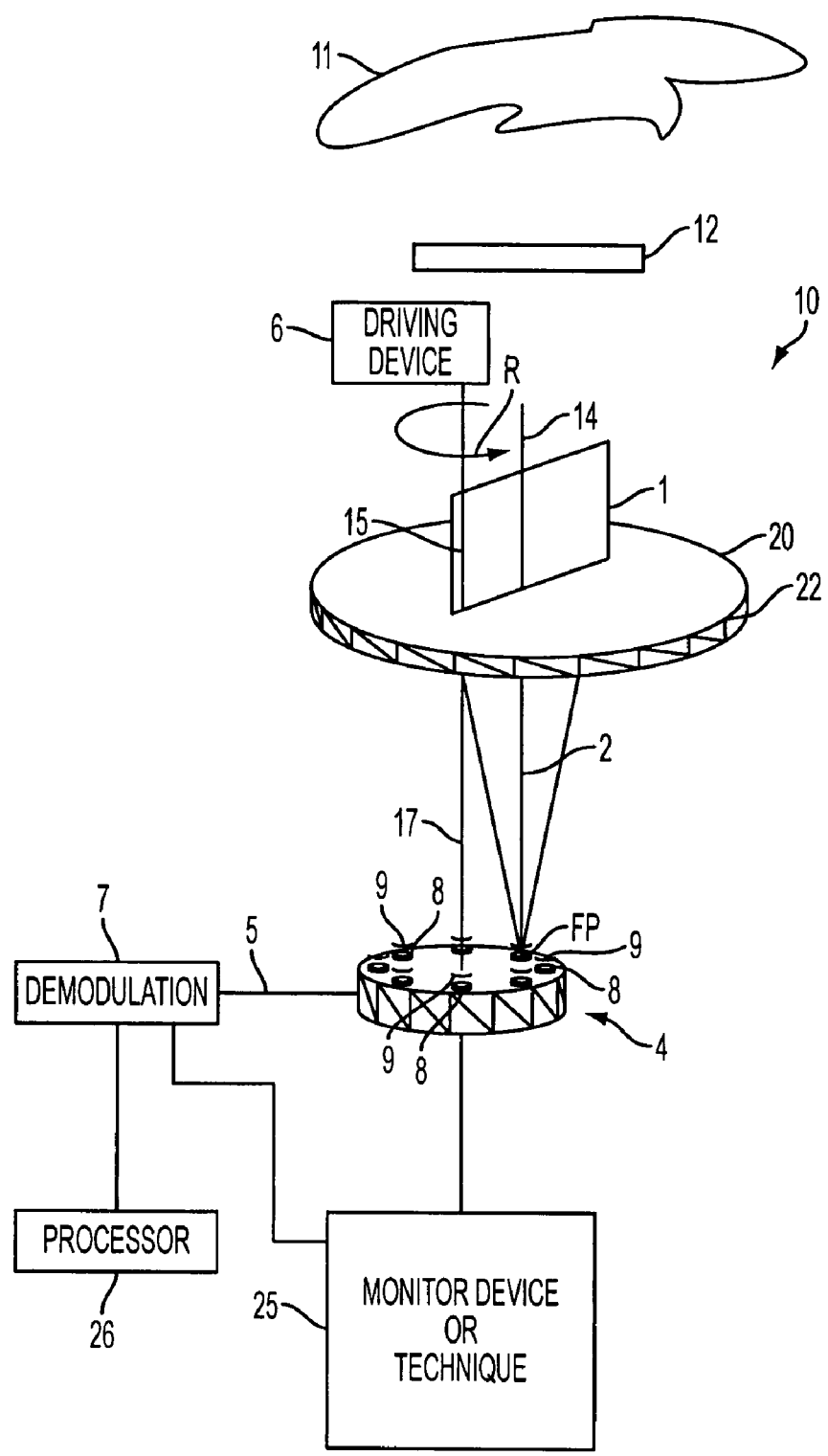
FIG. 5 schematically illustrates an embodiment of the present invention system for remote sensing and analyzing spectral properties of targets, wherein a light gathering device collects, focuses, and directs radiation emitted by the species or target to be detected or analyzed to an array of detectors, wherein a folding optical element is not necessarily included.

Next, turning to FIG. 5, FIG. 5 schematically illustrates an embodiment of the present invention system for remote sensing and/or analyzing spectral properties of targets as a means to detect and identify them. The light gathering device 20 is again a lens 22. In this embodiment, the lens has a central axis focus 14. Spectrally discriminating optical elements 9 are placed in front of or in the optical path of at least some of the detectors 8 for spectrally resolving the collected radiation. Some examples of spectrally discriminating optical elements 9 include, but not limited thereto, bandpass filters, notch filters, long and short pass filters, diffraction filters, polarizer filters, etc. This lens 22 is spun, as shown by the arrow of rotation referenced as R, around an optically off-center axis 15 of the lens by the driving device 6 coinciding with the central rotational axis 17 of the detector array 4 to modulate and distribute the radiation to the individual detectors 8. Alternatively, but not shown, the lens 22 and the detector array 4 can be arranged in a similar fashion, but the lens 22 can be fixed and the detector array 4 can be rotated about its central rotational axis 17 by the driving device 6 to produce the desired modulation (or both the lens and array can spin). The aperture device 12 is optional when desired or required and can be placed on either the target side (front) of the light gathering device 22 or behind the light gathering device, and can be either stationary or rotating with the light gathering device 22 or with the detector array 4.

Figure 6:
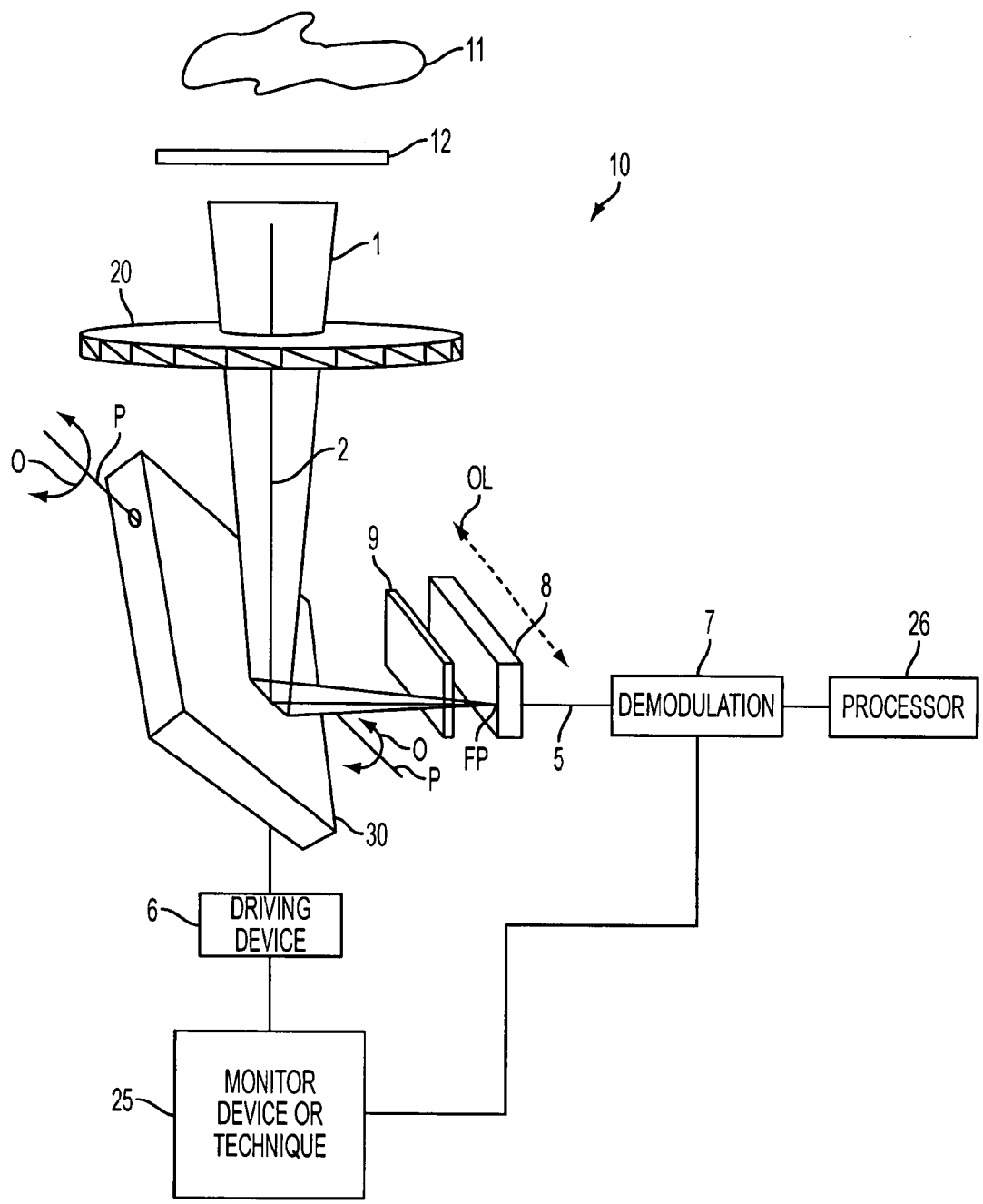
FIGS. 6 and 7 generally correspond with FIGS. 1 and 2, respectively, and schematically illustrate embodiments of the present invention system for remote sensing and analyzing spectral properties of targets with the notable feature of oscillation around a pivot (rather than rotation or spinning) which thereby provides the relative movement between the detector array and light gathering device or folding optical element.

Next, referring to FIGS. 6-7, FIGS. 6 and 7 generally correspond with FIGS. 1 and 2, respectively, and schematically illustrate embodiments of the present invention system for remote sensing and/or analyzing spectral properties of targets as a means to detect and identify them with the notable feature of angular oscillation around a pivot (as opposed to spinning or rotation) which thereby provides the relative movement between the detector array and light gathering device or folding optical element. Turning to FIG. 6, the folding optical device 30 (e.g., mirror) or light gathering device 20 (e.g., lens) oscillates angularly about a pivot point P or pivot axis (such a pivot axis is not necessarily coincident with the optical axis of the folding optical device) as indicated by arrow referenced as O. Alternatively, the linear detector array 4 may oscillate laterally along a line connecting the centers of the detectors, as shown by the dashed arrow referenced as OL. Moreover, it is conceivable that both the optical device 30 or light gathering device 20 and linear detector array 4 may oscillate (not shown). Accordingly, it should be appreciated that aspects as discussed throughout this document can be equally or substantially applied to FIG. 6. The aperture device 12 is optional when desired or required and can be placed on either the target side (front) of the light gathering device 20 or behind the light gathering device, and can be either stationary or oscillate with the folding optical element 22 as necessary for the aperture to track the beam.

Figure 7A:
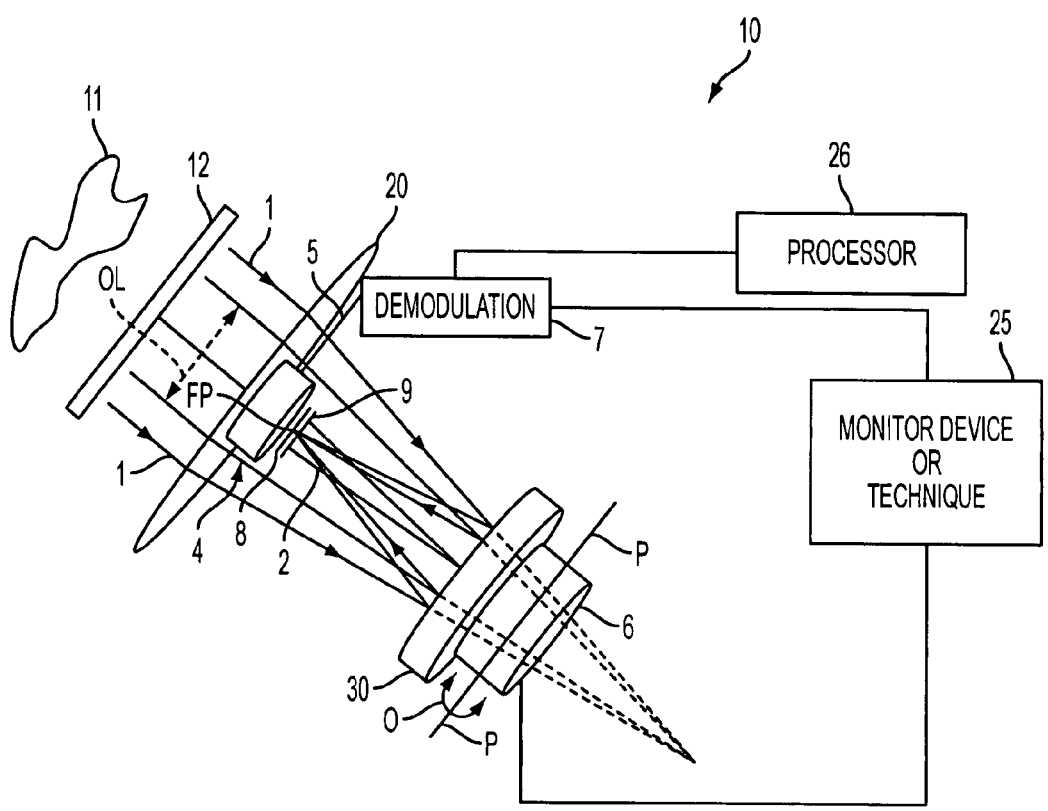
Figure 7B:
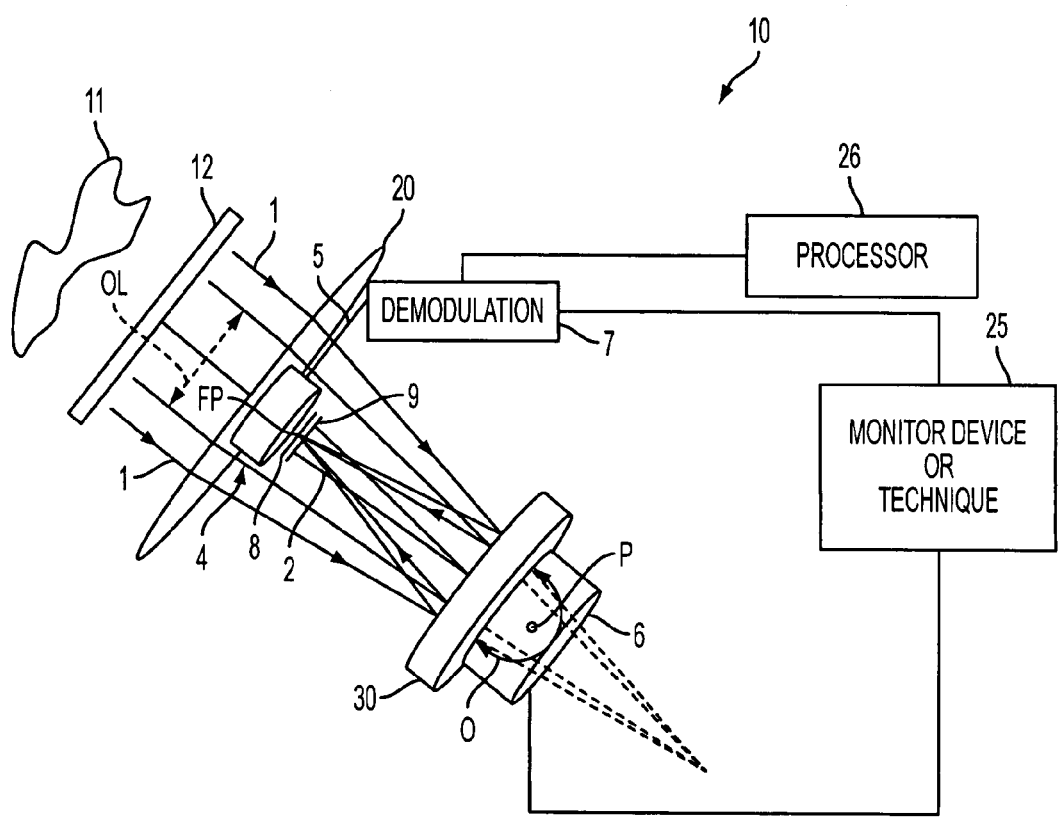

Turning to FIGS. 7(A)-(B) the folding optical device 30 (e.g., mirror) oscillates angularly about a pivot point P or pivot axis as indicated by arrow referenced as O. The mirror may be tilted at a small-reflection angle as shown in FIGS. 7(A)-(B) or may be perpendicular to the optical axis of the light gathering device 20 when in its neutral position. As schematically shown in FIG. 7(A), the pivot point P or pivot axis is aligned substantially parallel with the paper as illustrated. Alternatively, the linear detector array 4 may oscillate laterally along a line connecting the centers of the detectors, as shown by the dashed arrow referenced as OL. Whereas, as schematically shown in FIG. 7(B), the pivot point P or pivot axis is aligned perpendicular to the paper as illustrated. Alternatively, the linear detector array 4 may oscillate laterally along a line connecting the centers of the detectors, as shown by the dashed arrow referenced as OL. Moreover, it is conceivable that both the folding optical device 30, and linear detector array 4 may oscillate (not shown). Accordingly, it should be appreciated that aspects as discussed throughout this document can be equally or substantially applied to FIG. 7. The aperture device 12 is optional when desired or required and can be placed on either the target side (front) of the light gathering device 20 or behind the light gathering device, and can be either stationary or oscillate with the folding optical element 22.

Figure 8:
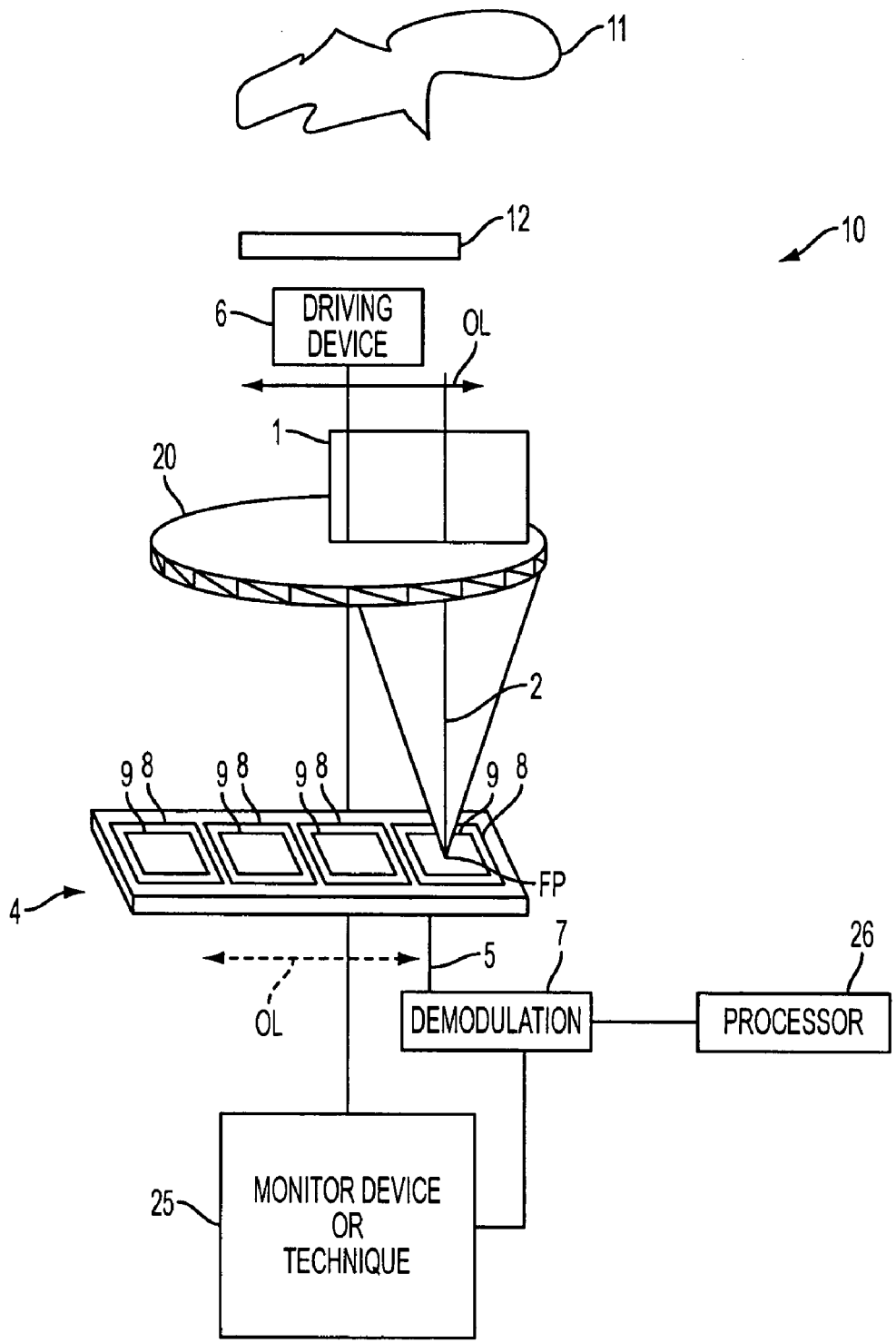
FIGS. 8 and 9 generally correspond with FIGS. 4 and 5, respectively, and schematically illustrate embodiments of the present invention system for remote sensing and analyzing spectral properties of targets with the notable feature of linear oscillation (rather than rotation or spinning) which thereby provides the relative movement between the detector array and light gathering device or folding optical element.
Figure 9:
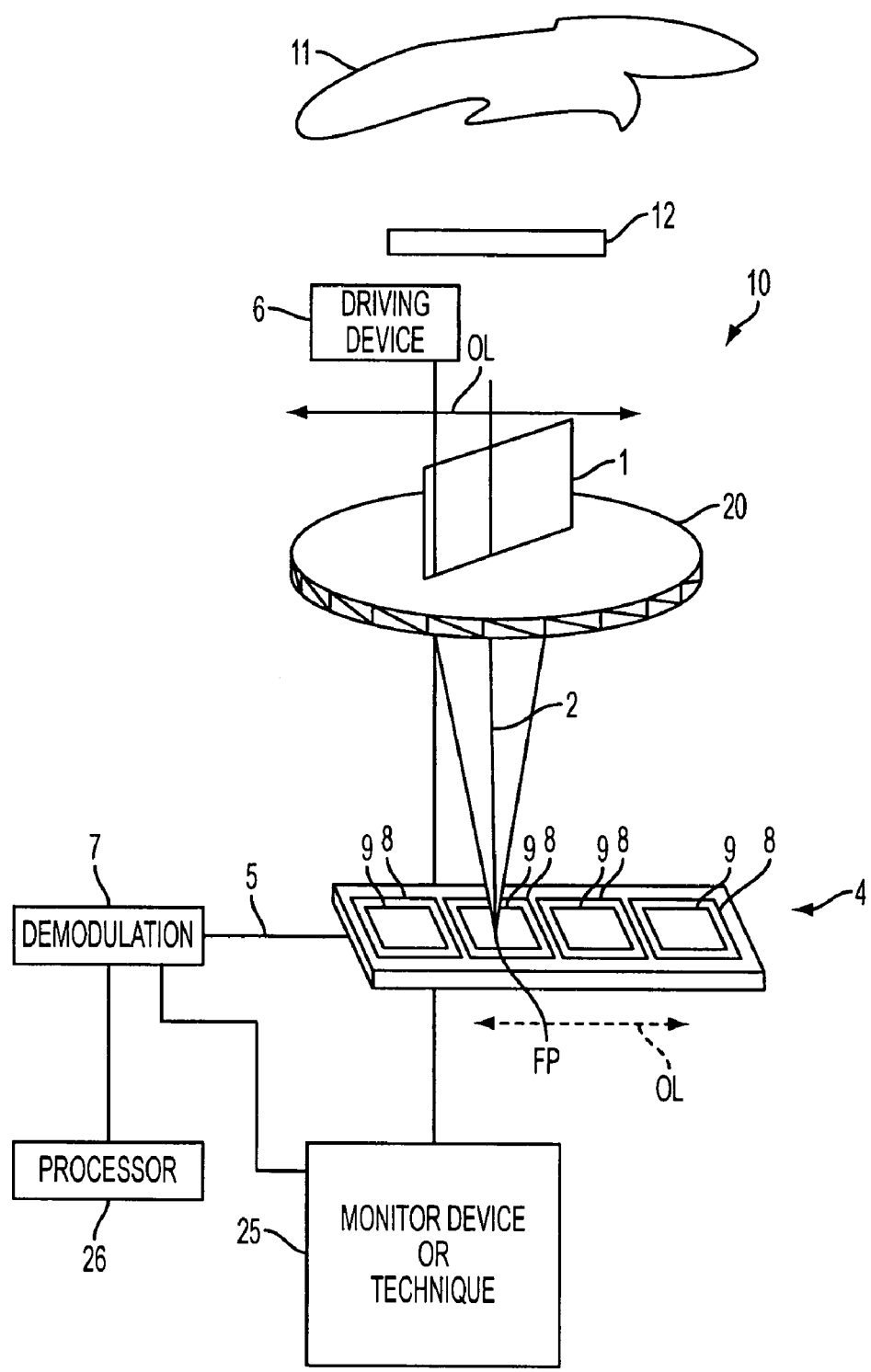

Next, referring to FIGS. 8 and 9, FIGS. 8 and 9 generally correspond with FIGS. 4 and 5, respectively, and schematically illustrate embodiments of the present invention system for remote sensing and/or analyzing spectral properties of targets as a means to detect and identify them with the notable feature of linear oscillation of the light gathering device 20 along a line that is parallel to the line connecting the centers of the detectors 8 on the array 4 (as opposed to spinning or rotation) which thereby provides the relative movement between the detector array and light gathering device or folding optical element. The light gathering device 20 (e.g., lens) oscillates laterally as indicated by arrow referenced as OL. Alternatively, the linear detector array 4 may oscillate laterally along a line connecting the centers of the detectors 8, as shown by the dashed arrow referenced as OL. Moreover, it is conceivable that both the optical device or light gathering device and linear detector array may oscillate (not shown). Accordingly, it should be appreciated that aspects as discussed herein can be equally applied to FIGS. 8 and 9. The aperture device 12 is optional when desired or required and can be placed on either the target side (front) of the light gathering device 20 or behind the light gathering device, and can be either stationary or oscillating with the light gathering device 20 or with the detector array 4.

Applicable for, but not required thereto, all of the distribution methods and systems described herein, nearly 100% of the desired incoming signal is delivered to the detectors 8 and, with aperturing each detector 8 views nearly the same scene even when the sensor is in motion as may be the case when operated while hand-carried by a person, or operated from a vehicle such as a car, helicopter, robot, unmanned air vehicle and the like.

In addition to distribution, modulation of the incoming radiation is achieved using the described method and system herein. In an embodiment, signal from a detector when the mirror, lens, or detector array is rotated to a position such that the focal point does not coincide with a detector provides a reference, or off-signal, while signal due to incoming radiation in the FOV, or the on-signal, is achieved when the focal point is aligned with the detector. However, to ensure a stable reference signal, off-axis incoming radiation must be blocked, or apertured, to prevent back reflection to a detector in the reference portion of the cycle of modulation or exposure to undesired components in the target areas. This blocking may be achieved with masks on the lens or the moving mirror (e.g., a mask may consist of an opaque disk with a hole located such that rays that are part of the incoming radiation 1 are transmitted unobstructed whereas the undesired off-axis rays are blocked), or aperturing devices, such as a honeycomb structure, placed in front of or behind the lens. This non-reflecting mask or radiation blocking aperture is placed on or near either side of the lens, mirror, or near the detectors in a manner to prevent radiation from outside the sensor from being reflected to each detector successively for a sufficient portion of the cyclical period to acquire a stable reference (typically a small fraction of a single rotation or oscillation period). With this mask or aperture, the incoming radiation 1 reaches a single detector as the desired signal and any other radiation from outside the sensor is not incident on that detector for some masked portion of the cycle; thus, a stable differential measurement may be achieved.

Frequently, optical filters, which also may radiate (mostly in the far infrared range of the spectrum) to the detectors, are mounted in front of the detectors; similarly, other parts of the sensor may radiate to the detectors; however, since the radiation emitted by the filters or components of the sensor itself, is not modulated using this method, the undesired radiation signal from the filters or the sensor may be separated from the desired incoming signal. The modulation frequency as experienced by any of the detectors is identical to the mirror or lens spinning, mirror-facet passing, or mirror or lens oscillating frequency if the motional element cycles at a constant rate. The modulation frequency of each detector can also be controlled actively by employing a stepper motor, linear motor or encoded analog motor as the motive element. Thus, when the angular frequency of the mirror or the detectors is actively controlled and varies, either during each cycle or from cycle to cycle, the actual modulation frequency is known.

Alternatively, rather than a stepper motor, linear or encoder motor, by monitoring the phase and frequency of the mirror, the time at which each detector is exposed to the target area is known and the signal associated with that event can be recorded, whereas signal at other times can either be rejected or recorded separately as a reference. As a result, a monitoring technique or method is achieved.

Once the radiation is distributed and modulated, the detector response to the incoming radiation must be determined. Typically, analog lock-in amplifiers are optimized for accurate demodulation of signals with a 50% duty cycle modulation. The attainable signal duty cycle associated with the described distribution and modulation method when using an equal dwell time per sensor is approximately 100%/n where n is the number of detectors. Thus, a demodulation method matched to this signal pattern is preferred. Up to two analog to digital (A/D) converters are used to monitor the (on) signal of two adjacent detectors while another converter may be required (depending on geometry) to monitor the (off) reference state of a non-illuminated detector. Two A/D converters may be necessary for monitoring the (on) signal of two adjacent detectors because, as the focal point location is changed, a portion of the focused signal can fall on two adjacent detectors for detector arrays where the interdetector spacing is significantly less than the focused beam size. These multiple A/D channels may be implemented with a single A/D converter with an input channel multiplexer. Samples of the detector signals are taken while radiation is focused on them. The decision to monitor a detector can be based on the output of a stepper motor controller, linear motor controller or an encoder. Reference samples, possibly acquired at a slower sample rate, are obtained from a detector preceding exposure to focused radiation. A microprocessor can then be used to compute the difference of the weighted averages of the (on and off) signals of each detector, providing an output proportional to the intensity of light reaching each detector from the target.

As can be applied to the various embodiments discussed throughout this document, the processor 26 or the like receives output signals from the detector array 4 and/or demodulation device 7 to detect and/or identify said targets and/or chemical species 11. Having detected the targets this spectral information can be utilized for a variety of applications, including but not limited thereto, the following: environmental and atmospheric monitoring, such as pollution control including but not limited to factory emission, vehicle emission, etc., military applications for detecting threat chemical gases, anti-terrorist applications for detecting of threat chemical gases, in industrial applications to monitor and control chemical processes including but not limited to quality control, process progress, safety, etc., in the oil industry to monitor and control oil or gas leaks, in the pharmaceutical industry to monitor and control medicine production processes, building security applications to monitor the buildup of various gases. The system can be at least partially or entirely disposed in a module or housing that is defined as either a: hand held device, portable device, fixed location mounted, vehicle mounted, robotic mounted and/or personnel mounted, or combination thereof.

The following patents, patent applications and publications are hereby incorporated by reference herein in their entirety:

U.S. Pat. No. 6,111,248 to Melendez et al, entitled "Self-Contained Optical Sensor System;"

U.S. Pat. No. 5,930,027 to Mentzer et al., entitled "Digitally Controlled Fiber Optic Light Modulation System;"

U.S. Pat. No. 5,585,622 to Durst et al., entitled "Optical Sensor with Mirror Toggling;"

U.S. Pat. No. 5,338,933 to Reeves et al., entitled "Scanning Optical Sensor;"

U.S. Pat. No. 4,980,547 to Griffin, entitled "Light Distribution and Detection Apparatus;"

U.S. Pat. No. 4,778,988 to Henderson, entitled "Displacement Detection;"

U.S. Pat. No. 4,669,817 to Mori, entitled "Apparatus for Time-Sharing Light Distribution;"

International Publication WO 00/55602 to Laufer, entitled "Passive Remote Sensor of Chemicals;"

U.S. Pat. No. 5,479,258 to Hinnrichs et al., entitled "Image Multispectral Sensing;"

U.S. Pat. No. 5,128,797 to Sachse et al., entitled "Non-Mechanical Optical Path Switching and its Application to Dual Beam Spectroscopy Including Gas Filter Correlation Radiometry;"

U.S. Pat. No. 4,790,654 to Clarke, entitled "Spectral Filter;"

U.S. Pat. No. 3,955,891 to Knight et al., entitled "Correlation Spectrometer;"

U.S. Pat. No. 6,057,923 to Sachse entitled "Optical Path Switching Based Differential Absorption Radiometry for Substance Detection;"

U.S. Pat. No. 5,210,702 to Bishop et al. entitled "Apparatus for Remote Analysis of Vehicle Emissions"

U.S. Pat. No. 5,319,199 to Stedman, entitled "Apparatus for Remote Analysis of Vehicle Emissions;"

U.S. Pat. No. 5,371,367 to DiDomenico et al. entitles "Remote Sensor Device for Monitoring Motor Vehicle Exhaust Systems"

U.S. Pat. No. 5,401,967 to Stedman entitled "Apparatus for Remote Analysis of Vehicle Emissions;"

U.S. Pat. No. 5,489,777 to Stedman entitled "Apparatus for Remote Analysis of Vehicle Emissions Using Reflective Thermography;"

U.S. Pat. No. 5,498,872 to Stedman entitled "Apparatus for Remote Analysis of Vehicle Emissions;"

U.S. Pat. No. 6,064,488 to Brand et al. entitled "Method and Apparatus for in Situ Gas Concentration Measurement;"

U.S. Pat. No. 5,886,247 to Rabbett entitled "High Sensitivity Gas Detection;"

G. Laufer, A. Ben-David, Optimized Differential Absorption Radiometer (DAR) for Remote Sensing of Chemical Effluents, App. Opt., 41, 2263-2273, 2002; and S. K. Holland, R. H. Krauss, G. Laufer, Demonstration and Evaluation of an Uncooled $LiTaO_3$ Detector Based Differential Absorption Radiometer for Remote Sensing of Chemical Effluents, to be published, Opt. Eng., 2004.

In summary, the present invention provides a low-cost, robust and simple system and method for remote sensing and analyzing spectral properties of targets as a means to detect and identify them.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A system for remote sensing and analyzing spectral properties of at least one target and/or chemical species, said system comprising:
   a light gathering device that collects and focuses incoming radiation emitted and/or absorbed and/or scattered by the target and/or chemical species to be analyzed;
   a folding optical element for directing said collected and focused radiation from said light gathering device to at least one of a plurality of detectors;
   at least one spectrally discriminating optical element in front of at least some of said detectors for spectrally resolving said collected radiation;
   said detectors, in relative movement with said folding optical element, producing an output signal; and
   a driving device to produce said relative movement;
   a device or method to monitor phase and frequency of the relative movement; and
   a demodulation device, synchronous with said driving device, to demodulate said output signal produced by said detectors.

2. The system of claim 1, wherein said light gathering device comprises a lens.

3. The system of claim 1, wherein said detectors comprise an array.

4. The system of claim 3, wherein said array comprises at least one of a curved array, circular array, ring array, or linear array.

5. The system of claim 3, wherein said array is rotated or oscillated to provide said relative movement.

6. The system of claim 3, wherein said array includes at least one gap, said at least one gap defined as without any active detector and towards which light can be directed when array is not operational.

7. The system of claim 1, wherein said spectrally discriminating optical element comprises at least one of bandpass filters, notch filters, long and short pass filters, diffraction filters or polarizer filters or combination of at least one of a bandpass filter, notch filter, long pass filter, short pass filter or polarizer filter.

8. The system of claim 1, wherein said folding optical element comprises a multifaceted mirror.

9. The system of claim 1, wherein said folding optical element is tilted.

10. The system of claim 9, wherein the tilt is a large reflection angle, wherein large reflection angle provides ability to project the axial ray away from incoming radiation that is focused by the light gathering device.

11. The system of claim 10, wherein said folding optical element is rotated by said driving device to provide said relative movement.

12. The system of claim 10, wherein said plurality of detectors is rotated around folding optical element by said driving device to provide said relative movement.

13. The system of claim 9, wherein the tilt is a small reflection angle, wherein small reflection angle provides ability to project the axial ray toward incoming radiation that is focused by the light gathering device.

14. The system of claim 13, wherein said folding optical element is rotated by said driving device to provide said relative movement.

15. The system of claim 13, wherein said plurality of detectors is rotated by said driving device to provide said relative movement.

16. The system of claim 13, wherein said plurality of detectors is rotated around the line of the axial ray near the focal point by said driving device to provide said relative movement.

17. The system of claim 1, wherein said folding optical element is rotated or oscillated to provide said relative movement.

18. The system of claim 1, wherein said folding optical element comprises a mirror tilted and is located between said plurality of detectors and said light gathering device.

19. The system of claim 1, wherein said folding optical element is angularly oscillated around a pivot relative to said detectors by said driving device to provide said relative movement.

20. The system of claim 19, wherein said folding optical element is tilted.

21. The system of claim 1, wherein said plurality of detectors is linearly oscillated relative to said folding optical element by said driving device to provide said relative movement.

22. The system of claim 21, wherein said folding optical element is tilted.

23. The system of claim 22, wherein said folding optical element is tilted at a large reflection angle.

24. The system of claim 1, wherein said driving device comprises at least one of a digitally or analog controlled motor.

25. The system of claim 1, further comprising an aperture device along the optical path from the target to said detectors to prevent off-axis incoming radiation from impinging on the detectors.

26. The system of claim 25, wherein said aperture device comprises an array of parallel optically transmitting channels or substantially parallel optically transmitting channels in front of said light gathering device.

27. The system of claim 26, wherein said array of parallel or substantially parallel optically transmitting channels is honeycomb structure.

28. The system of claim 25, wherein said aperture device comprises an array of parallel optically transmitting channels or substantially parallel optically transmitting channels behind said light gathering device.

29. The system of claim 28, wherein said array of parallel or substantially parallel optically transparent channels is honeycomb structure.

30. The system of claim 25, wherein said aperture device comprises a mask, whereby said mask allows radiation from said target to pass through to the currently illuminated detector(s) in the cycle sequence, whereby off-axis radiation is blocked or at least substantially blocked from the currently illuminated detector(s) and detector(s) selected to be monitored for generating their reference signal.

31. The system of claim 30, wherein said mask is defined as at least one opaque member with a hole or gap forming an aperture adapted to allow the radiation to pass there through.

32. The system of claim 31, wherein said opaque member is a disk, planar member, or substantially planar member, or member conforming to the general shape of the detector array surface, operating in front of said surface.

33. The system of claim 1, further comprising a processor wherein said processor receives output signals from said detectors and!or demodulation device to separate background effects and noise from output signal to provide a net output that represents the spectral characteristics of the target and use those characteristics to detect andlor identify said targets.

34. The system of claim 33, wherein said detected andlor identified targets are provided for at least one of: reducing or eliminating danger in public, private or military facilities or spaces or outdoors due to the presence of toxic chemicals, to allow control of chemical or medical manufacturing processes, or to allow control or monitoring of pollution or other processes due to plant or factory emission or other equipment.

35. The system of claim 33, wherein said system is at least partially disposed in a housing defined as hand held device, portable device, fixed location mounted, vehicle mounted, or robotic mounted or personnel mounted.

36. A system for remote sensing and analyzing spectral properties of at least one target and/or chemical species, said system comprising:
  a light gathering device that collects, focuses, and directs incoming radiation emitted and/or absorbed and/or scattered by the target and/or chemical species to be analyzed to one of a plurality of detectors;
  at least one spectrally discriminating optical element in front of at least some of said detectors for spectrally resolving said collected radiation;
  said detectors, in relative movement with said light gathering device, producing an output signal;
  a driving device to produce said relative movement between said light gathering device and said detectors;
  a device or method to monitor phase and frequency of the relative movement; and
  a demodulation device, synchronous with said driving device, to demodulate said output signal produced by said detectors.

37. The system of claim 36, wherein said detectors comprise an array.

38. The system of claim 37, wherein said array comprises at least one of a curved array, circular array, ring array, or linear array.

39. The system of claim 38, wherein said array includes at least one gap, said at least one gap defined as without any active detector and towards which light can be directed when array is not operational.

40. The system of claim 36, wherein:
  said detectors comprise an array; and
  said light gathering device comprises a lens with an off-axis focus spinning around its own geometrically central axis, which is aligned with the central axis of said detector array, such that said source radiation focuses on said elements of said detector array, in a sequence.

41. The system of claim 40, said sequence is defined by the radiation focusing on one of said individual detectors at a time.

42. The system of claim 40, said sequence is defined by the radiation focusing on at least a plurality of said individual detectors one at a time or a plurality at a time.

43. The system of claim 36, wherein:
said detectors comprise an array; and
said light gathering device comprises a lens spinning around an axis which is off the geometrical center and that coincides with the geometrically central axis of said detector array such that said radiation focuses on said elements of said detector array, in a sequence.

44. The system of claim 43, said sequence is defined by the radiation focusing on one of said individual detectors at a time.

45. The system of claim 43, said sequence is defined by the radiation focusing on at least a plurality of said individual detectors one at a time or a plurality at a time.

46. The system of claim 36, wherein:
said detectors comprise an array; and
said light gathering device comprises a fixed lens with an off-axis focus and said detector array is rotated around the geometrically central axis of said lens by said driving device such that said radiation focuses on said elements of said detector array, in a sequence.

47. The system of claim 46, said sequence is defined by the radiation focusing on one of said individual detectors at a time.

48. The system of claim 46, said sequence is defined by the radiation focusing on at least a plurality of said individual detectors one at a time or a plurality at a time.

49. The system of claim 36, wherein:
said detectors comprise an array; and
said light gathering device comprises a fixed lens and said detector array is rotated around an axis offset from but parallel to the geometrically central axis of said lens by said driving device such that said radiation focuses on said elements of said detector array, in a sequence.

50. The system of claim 49, said sequence is defined by the radiation focusing on one of said individual detectors at a time.

51. The system of claim 49, said sequence is defined by the radiation focusing on at least a plurality of said individual detectors one at a time or a plurality at a time.

52. The system of any one of claims 40, 43, 46, or 49, wherein said array comprises a circular array.

53. The system of claim 36, wherein:
said detectors comprise an array; and
said light gathering device comprises a lens linearly oscillating relative to said detector array such that said radiation focuses on said elements of said detector array, in a sequence.

54. The system of claim 53, said sequence is defined by the radiation focusing on one of said individual detectors at a time.

55. The system of claim 53, said sequence is defined by the radiation focusing on at least a plurality of said individual detectors one at a time or a plurality at a time.

56. The system of claim 36, wherein:
said detectors comprise an array; and
said light gathering device comprises a lens and said detector array oscillates linearly relative to the said lens such that said radiation focuses on said elements of said detector array, in a sequence.

57. The system of claim 56, said sequence is defined by the radiation focusing on one of said individual detectors at a time.

58. The system of claim 56, said sequence is defined by the radiation focusing on at least a plurality of said individual detectors one at a time or a plurality at a time.

59. The system of any one of claims 53 or 56, wherein said array comprises a linear array or curved array.

60. The system of claim 36, wherein said driving device comprises at least one of a digital or analog controlled motor.

61. The system of claim 36, further comprising an aperture device along the optical path from the target to said detectors to prevent off-axis incoming radiation from impinging on the detectors.

62. The system of claim 61, wherein said aperture device comprises an array of parallel optically transparent channels or substantially parallel optically transparent channels in front of said light gathering device.

63. The system of claim 62, wherein said array of optically transparent parallel or substantially parallel channels is honeycomb structure.

64. The system of claim 61, wherein said aperture device comprises an array of parallel optically transparent channels or substantially parallel optically transparent channels behind said light gathering device.

65. The system of claim 64, wherein said array of parallel optically transparent channels is honeycomb structure.

66. The system of claim 61, wherein said aperture device comprises a mask, whereby said mask allows radiation from said target to pass there through to currently illuminated detector(s) in the cycle sequence, whereby off-axis radiation is blocked or at least substantially blocked from the currently illuminated detector(s) and detector(s) selected to be monitored for generating their reference signal.

67. The system of claim 66, wherein said mask is defined as at least one opaque member with a hole or gap forming an aperture adapted to allow the radiation to pass there through.

68. The system of claim 67, wherein said opaque member is a disk, planar member, or substantially planar member, or member conforming to the general shape of the detector array surface, operating in front of said surface.

69. The system of claim 36, wherein said spectrally discriminating optical element comprises at least one of bandpass filters, notch filters, long and short pass filters, diffraction filters or polarizer filters or combination of at least one of a bandpass filter, notch filter, long pass filter, short pass filter or polarizer filter.

70. The system of claim 36, further comprising a processor wherein said processor receives output signals from said detectors and/or demodulation device to separate background effects and noise from output signal to provide a net output that represents the spectral characteristics of the target and use those characteristics to detect andlor identify said targets.

71. The system of claim 70, wherein said detected andlor identified targets are provided for at least one of: reducing or eliminating danger in public, private or military facilities or spaces or outdoors due to the presence of toxic chemicals, to allow control of chemical or medical manufacturing processes, or to allow control or monitoring of pollution or other process due to plant or factory emission or other equipment.

72. The system of claim 70, wherein said system is at least partially disposed in a housing defined as hand held device, portable device, fixed mounted location, vehicle mounted, robotic mounted or personnel mounted.

73. A method for remote sensing and analyzing spectral properties of at least one target and/or chemical species, said method comprising:

collecting and focusing incoming radiation emitted and/or absorbed and/or scattered by the target and/or chemical species to be analyzed, said collecting and focusing being conducted from a gathering location;

directing said focused radiation, said directing being conducted at a directing location;

spectrally analyzing said collected radiation at a spectral analysis location, said spectral analysis produces spectral signature that can be used to identify target;

detecting said directed and spectrally analyzed radiation at a detecting location, wherein said directing location and said detecting location is in relative movement from one another, said detection producing an output signal;

monitoring the phase and frequency of the relative movement; and demodulating said output signal.

74. The method of claim 73, wherein said collecting and focusing are accomplished using a lens.

75. The method of claim 73, wherein said collected radiation is spectrally analyzed by a plurality of at least one of bandpass filters, notch filters, long and short pass filters, diffraction filters or polarizer filters or combination of at least one of a bandpass filter, notch filter, long pass filter, short pass filter or polarizer filter.

76. The method of claim 73, wherein said detecting is accomplished by a plurality of detectors.

77. The method of claim 76, wherein said detectors comprise an array.

78. The method of claim 77, wherein said array includes at least one gap, said at least one gap defined as without any active detector and towards which light can be directed when array is not operational.

79. The method of claim 73, wherein said directing is accomplished by a folding optical element.

80. The method of claim 79, wherein said folding optical element is tilted.

81. The method of claim 80, wherein the tilt is a large reflection angle, wherein the large reflection angle provides ability to project the axial ray away from the incoming radiation that is focused by the light gathering device.

82. The method of claim 80, wherein the tilt is a small reflection angle, wherein the small reflection angle provides ability to project the axial ray toward the incoming radiation that is focused by the light gathering device.

83. The method of claim 79, wherein said folding optical element comprises a reflecting mirror or multifaceted mirror.

84. The method of claim 79, wherein said folding optical element is rotated or oscillated.

85. The method of claim 79, wherein:

said detecting is accomplished by a plurality of detectors forming an array; and said detector array is rotated around said tilted folding optical element.

86. The method of claim 79, wherein:

said detecting is accomplished by a plurality of detectors forming an array; and said detector array is linearly oscillated relative to said tilted folding optical element.

87. The method of claim 73, wherein said relative movement is accomplished by a driving device.

88. The method of claim 87, wherein said driving device comprises at least one of a digitally or analog controlled motor.

89. The method of claim 73, wherein:

said directing is accomplished by a folding optical element; and said detecting is accomplished by a plurality of detectors.

90. The method of claim 89, further comprising aperturing the incoming radiation to prevent off-axis incoming radiation from impinging on the detectors.

91. A method for remote sensing and analyzing spectral properties of at least one target and/or chemical species, said method comprising:

collecting, focusing, and directing incoming radiation emitted and/or absorbed and/or scatterd by the target and/or chemical species to be analyzed, said collecting, focusing, and directing being conducted from a gathering location;

spectrally analyzing said collected radiation at a spectral analysis location, said spectral analysis produces spectral signature that can be used to identify target;

detecting said directed and spectrally analyzed radiation at a detecting location, wherein said gathering location and said detecting location is in relative movement from one another, said detection producing an output signal;

monitoring the phase and frequency of the relative movement; and demodulating said output signal.

92. The method of claim 91, wherein said collecting, focusing, and directing are accomplished using a lens.

93. The method of claim 92, wherein said collected radiation is spectrally analyzed by at least one of bandpass filters, notch filters, long and short pass filters, diffraction filters, or polarizer filters or combination of at least one of bandpass filter, notch filter, long pass filter, short pass filter, diffraction filters, or polarizer filter or combination of a bandpass filter, notch filter, long pass filter, short pass filter and polarizer filter.

94. The method of claim 91, wherein said detecting is accomplished by a plurality of detectors.

95. The method of claim 94, wherein said detectors comprise an array.

96. The method of claim 95, wherein said array comprises at least one of a curved array, circular array, ring array, or linear array.

97. The method of claim 95, wherein said array includes at least one gap, said at least one gap defined as without any active detector and towards which light can be directed when array is not operational.

98. The method of claim 91, wherein:

said collecting, focusing, and focusing are accomplished using a lens; and said detecting is accomplished by a plurality of detectors.

99. The method of claim 98, wherein:

said detectors comprise a detector array; and said lens with an off-axis focus spinning around its own geometrically central axis, which is aligned with the central axis of said detector array, such that said source radiation focuses on the elements of the detector array, in a sequence.

100. The method of claim 98, wherein:

said detectors comprise a detector array; and said lens spinning around an axis that is off its geometrical center but that coincides with the geometrically central axis of said detector array such that said radiation focuses on the elements of the detector array, in a sequence.

101. The method of claim 98, wherein:

said detectors comprise an array; and said lens is fixed with an off-axis focus and said detector array is rotated around the geometrically central axis of said lens by said driving device such that said radiation focuses on the elements of the detector array, in a sequence.

102. The method of claim 98, wherein:

said detectors comprise an array; and said lens is fixed and said detector array is rotated around an axis offset from but parallel to the geometrically central axis of said lens by said driving device such that said radiation focuses on the elements of the detector array, in a sequence.

103. The method of claim 98, wherein:

said detectors comprise an array; and said light gathering device comprises a lens linearly oscillating relative to said detector array such that said radiation focuses on the elements of the detector array, in a sequence.

104. The method of claim 98, wherein:

said detectors comprise an array; and said light gathering device comprises a lens and said detector array oscillates linearly relative to the said lens such that said radiation focuses on the elements of the detector array, in a sequence.

105. The method of claim 98, wherein said relative movement is accomplished by a driving device.

106. The method of claim 98, further comprising aperturing the incoming radiation to prevent off-axis incoming radiation from impinging on the detectors.

* * * * *